United States Patent [19]

Wilson

[11] Patent Number: 4,752,385
[45] Date of Patent: Jun. 21, 1988

[54] LIQUID CHROMATOGRAPH

[75] Inventor: James B. Wilson, Nailsea, England

[73] Assignee: U.S. Philips Corporation, New York, N.Y.

[21] Appl. No.: 908,465

[22] Filed: Sep. 17, 1986

[30] Foreign Application Priority Data

Sep. 18, 1985 [GB] United Kingdom ............... 8523014

[51] Int. Cl.$^4$ .................. B01D 15/08; F04B 49/00
[52] U.S. Cl. .................. 210/101; 210/198.2; 210/656; 417/18
[58] Field of Search .................. 210/101, 198.2, 656; 417/18

[56] References Cited

U.S. PATENT DOCUMENTS

| | | | |
|---|---|---|---|
| 3,816,029 | 6/1974 | Bowen et al. | 417/539 |
| 4,359,312 | 11/1982 | Funke et al. | 417/18 |
| 4,422,942 | 12/1983 | Allington | 210/101 |
| 4,448,692 | 5/1984 | Nakamoto et al. | 210/198.2 |
| 4,492,524 | 1/1985 | Koch et al. | 210/101 |

Primary Examiner—Richard V. Fisher
Assistant Examiner—Richard D. Jordan
Attorney, Agent, or Firm—Paul R. Miller

[57] ABSTRACT

The liquid chromatograph comprises a multiple piston pump (1) which is arranged so that the delivery strokes of two pistons overlap to such an extent that for all designed liquid delivery pressures and compressibilities no period exists when no piston is delivering liquid. Thus for all other than worst case conditions there are periods in each pump cycle when two pistons are delivering liquid. The start of these periods is detected by the pressure increase produced at the outlet of the pump and measured by a pressure transducer (5). The output of the pressure transducer is fed via path (14) to a motor drive circuit (10) which controls a motor (4) which drives the pump (1) via a shaft (3) so that the speed of advance of the pistons is halved until one of the pistons ceases delivery. Consequently a relatively pulse free liquid flow is produced by the pump with a relatively simple motor speed control system.

14 Claims, 5 Drawing Sheets

LIQUID CHROMATOGRAPH

DESCRIPTION

The invention relates to a liquid chromatograph comprising a multiple piston reciprocating pump for delivering a liquid at a desired flow rate to a separating column, each piston being arranged, during its delivery stroke, to deliver liquid at the same rate as the others, wherein the pistons are arranged to have overlapping delivery strokes and are driven by a motor whose speed is controlled by a control arrangement.

In liquid chromatography systems, and in particular high performance liquid chromatographs (HPLC), the pump is required to have a flow capability covering the range of, typically, 1 $\mu$l to 30 ml/min, a minimum internal volume so that a solvent change at the inlet to the pump rapidly reaches the column input, minimum pulsation in flow/pressure since the stability of most detection systems is adversely affected by such pulsations, and a capability of delivering at a sufficient pressure to enable the required flow of solvent through all columns likely to be used. The discharge pressure may, typically, range between 5 and 400 Bar and a variety of solvents with compressibilities between 50 and $150 \times 10^{-6}$/Bar may be used.

A variety of pumping systems are available for use in HPLC, each of which have their own advantages and disadvantages. This invention relates to chromatographs in which reciprocating piston pumps are used. Such pumps can be divided into single and multiple piston pumps. Single piston pumps have the advantage of mechanical simplicity but pose greater difficulty in achieving low pulsation in flow/pressure of the delivered liquid. With multi piston pumps it is possible to arrange that, in theory, one piston is always delivering and thus pulsation is reduced. However, due to the high pressures involved there is a significant compression of the liquid and hence the instant at which any piston starts to deliver cannot be determined merely from the position of the piston as a degree of precompression, which varies with the particular solvent used, occurs before delivery commences and hence a drop in pressure will occur when one piston stops delivering before the other piston starts to deliver. One method of alleviating this problem is to monitor the pressure at the pump outlet and to increase the motor speed when the pressure falls thus minimising the period when no flow is produced by the pump and hence reducing the drop in pressure and the magnitude of the pulsations. However this requires a complex control system to drive the pump.

UK-A-2085980 discloses a liquid chromatograph as set forth in the opening paragraph which includes a regulating system for continuously varying the speed of the motor so that the pressure of the liquid conveyed remains at least approximately constant during each period.

It is an object of the invention to enable the provision of a liquid chromatograph pump having a relatively simple control system which is capable of producing an output flow of liquid having comparatively low pressure pulsation.

The invention provides a liquid chromatograph as set forth in the opening paragraph characterised in that the control arrangement is arranged to produce a control signal having a characteristic of a first constant value during a first period when the number m of the piston(s) is/are delivering liquid to the column so that the piston(s) advance at a first constant velocity and a second constant value during a second period when the number (m+1) pistons are delivering liquid to the column to cause the pistons to advance at a second constant velocity, the second constant velocity being m/(m+1) times the first constant velocity, where m is an integer and (m+1) is less than or equal to the total number of pistons provided in the pump.

By arranging that the delivery strokes of the pistons overlap there is never a period when no piston is delivering; only a first period when m piston(s) is/are delivering and a second period when (m+1) pistons are delivering and by providing a constant rate of advance a relatively constant flow, and hence constant delivery pressure, can be obtained merely by dividing the rate of advance of the pistons by (m+1)/m during the second period. Thus, if the start and finish of the second period can be determined, a relatively simple control arrangement can be used to control the rate of advance of the pistons, merely requiring a division of the rate of advance at appropriate times.

This can be contrasted with the position disclosed in UK-A-2085980 where because the pistons do not advance with a constant linear velocity for a constant angular velocity of the cam it is necessary to continuously vary the cam velocity in order to obtain a constant flow rate. This causes considerable complexity in the regulating system.

The pump may be a dual piston pump. In this case m=1 and the rate of advance of the pistons is halved when both pistons are delivering.

The start of the second period may be detected by monitoring the pressure of the liquid delivered by the pump, an increase in the pressure denoting the start of the second period.

This gives a precise indication of the start of the second period when (m+1) pistons are delivering and the instant of detection of increasing pressure can be used to divide the rate of advance of the pistons. This quickly brings the total flow rate back to the same value as when m pistons are delivering. It should be noted that while the instant when (m+1) pistons start to advance can also be easily detected, that instant cannot be used to control the speed of advance since at high delivery pressures significant precompression of the liquid takes place in the cylinder before delivery commences. The extent of the precompression will depend on the particular solvent being pumped, which may be continuously changing, and the pressure at which delivery takes place, which will depend on the column resistance and flow rate. Further it is not necessary to monitor the actual pressure since it is known that the flow rate will return to the desired value merely by dividing the rate of advance of the pistons by m/(m+1).

The end of the second period may be detected by monitoring the positions of the pistons. It is not necessary to detect pressure changes at the outlet of the pump to ascertain when one of the pistons ceases to deliver liquid since this is accurately known from the position of the piston, i.e. when the piston reaches top dead center it can no longer deliver liquid. There is no problem with precompression of the liquid at this end of the delivery cycle although the filling of the cylinder during the withdrawal of the piston may be affected by decompression, both of the liquid remaining in the cylinder and in the seals and other deformable parts.

The motor may drive the pistons through a cam arrangement. The cam arrangement may comprise a separate cam for each piston, the cams being mounted on or formed integrally with a common shaft.

A separate cam for each piston allows the pistons to be arranged side by side rather than being horizontally opposed. This simplified the mechanical arrangement of the combining means required to combine the liquid outlets of each cylinder for feeding to the column. It also allows more flexibility in designing the fill stroke of each piston.

The cam(s) may be profiled such that a constant angular velocity of the cam(s) produces a constant linear velocity of the delivering piston(s).

This enables a simplification of the control arrangement which simply has to ensure that the motor speed remains constant at one of two values depending on how many pistons are delivering. If the cam profiles are not formed in this manner the motor speed has to be varied to compensate for the cam characteristic. This could be achieved using a programmed memory, for example a programmable read only memory (PROM) which stores a representation of the speed correction required against cam angle to enable a constant rate of piston advance to be achieved. This enables the control arrangement to produce a constant output signal which is corrected for the cam characteristic by the contents of the PROM thus retaining a simple control arrangement but requiring a set up procedure at the manufacturing stage or if a cam is replaced.

The end of the second period may be detected by monitoring the positions of the pistons. The position of the pistons may be monitored by means of an encoder mounted on the shaft.

This enables the instant at which each of the pistons ceases to deliver liquid to be accurately detected and enables a signal to be produced to increase the speed of the motor when the end of said period is reached.

The pump may be driven by an electrical stepping motor, the characteristic of the control signal being its frequency, and during the second period in which $(m+1)$ pistons are delivering liquid the frequency of the pulses applied to the motor is divided by $(m+1)/m$.

Thus when the pump is a dual piston pump this enables the rate of advance to be halved using a simple control circuit which involves passing the stepping pulses through a binary divider during this period. This separates the control function for maintaining a constant flow rate from the control function which sets the desired flow rate for a particular analysis.

The invention is based on the principle that if the rate of advance of the pistons is constant, then the flow rate of the liquid must also be constant, and that provided that in the case of a two piston pump, it can be ensured that there is no period when neither pump is delivering, and that it can be determined when both pistons are delivering, a constant flow rate can be achieved merely by halving the rate of advance of the pistons for the period when both pistons are delivering. Consequently it is not necessary for the pressure to be continuously monitored and used as an input to the control circuit to continuously control the rate of advance of the pistons.

In the embodiment described the pressure is monitored and used to determine when both pistons start delivering but alternative procedures could be adopted, for example by detecting when the check valves at the outlets of the cylinders opened. In this case the control arrangement would not need an input which were pressure related.

An embodiment of the invention will now be described, by way of example, with reference to the accompanying drawings, in which.

Figure 1:
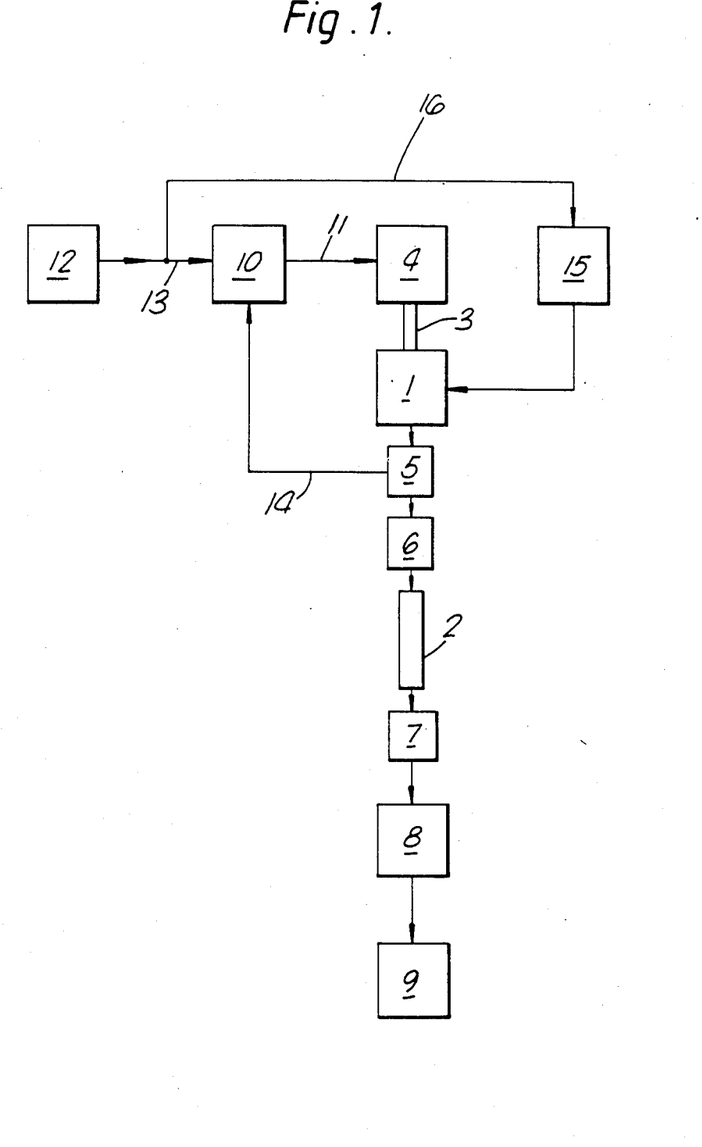
FIG. 1 shows in block schematic form a liquid chromatograph according to the invention.

FIG. 1 shows in block schematic form a liquid chromatograph which comprises a multiple piston pump 1 for pumping a liquid through a separating column 2. The pump 1 is coupled by a shaft 3 to a stepper motor 4 which drives the pump 1. A pressure transducer 5 monitors the pressure at the outlet of the pump 1 and also connected between the outlet of the pump 1 and in the inlet of the column 2 is a sample injector 6. The outlet of the column 2 is connected to a detector 7 which produces an electrical output which is fed to processing circuitry 8 which in turn drives a display device 9. The display device 9 may take any convenient form, for example a video display unit or a chart recorder. The stepper motor 4 is driven by a stepper motor drive circuit 10 which feeds stepping pulses at a desired rate to the stepper motor 4 over a path 11. The stepper motor drive circuit 10 receives a first input from an input unit 12 over a path 13. The input unit 12 may be a keyboard to allow the desired flow rate to be entered by an operator or may be any other arrangement which allows the operating parameters of the chromatograph to be set up. The stepper motor drive circuit 10 also receives a second input over a path 14 from the pressure transducer 5. The inlet of the pump 1 is fed from a solvent mixing arrangement 15 which is controlled by signals from the input unit 12 over a path 16.

In operation a desired flow rate is set up using the input unit 12 which produces signals which enable the stepper motor drive circuit 10 to produce stepping pulses to drive the stepper motor 4 at the appropriate speed to produce the desired flow rate when m pistons are delivering the liquid where $(m+1)$ is less than or equal to the total number of pump pistons. The pump is arranged so that the delivery strokes of the pistons overlap to such an extent that periods of non-delivery are eliminated under worst case conditions of flow rate, pressure and compressibility for which the system is designed. Consequently under all but the worst case conditions there will be a period in each cycle when $(m+1)$ pistons are delivering. At the start of this period the flow rate will increase by a factor $(m+1)/m$ and as a result the pressure at the pump outlet will increase. This pressure increase is detected by the pressure transducer 5 which produces a signal which is fed to the stepper motor drive circuit 10 over the path 14. This signal causes the stepper motor drive circuit 10 to divide the rate of the stepping pulses applied to the stepper motor 4 over the path 11 by $(m+1)/m$, thus reducing the rate of advance of the pistons. This reduces the flow rate to the desired value for the period when $(m+1)$ pistons are delivering. At the end of the period of overlapping delivery the rate at which the stepping pulses are applied to the stepper motor 4 is restored to the original value.

There are various possible ways of detecting the end of the period of overlapping delivery, for example a pressure drop at the outlet of the pump 1 can be detected by the pressure transducer 5. However, it is currently preferred to detect when each piston reaches top dead center after which no delivery from that cylinder can take place. This can be achieved by means of a shaft encoder where the pistons are driven by means of cams mounted on the shaft 3 driven by the stepper motor 4.

Figure 4:
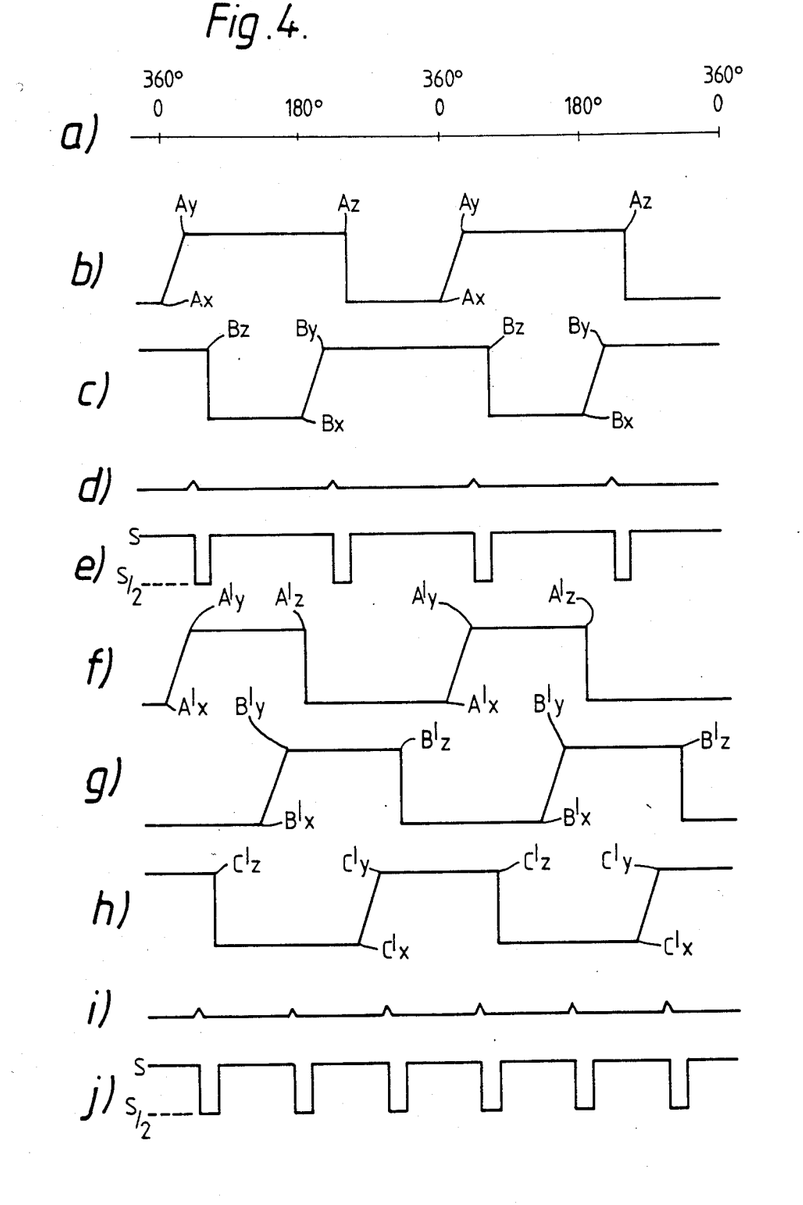
FIG. 4 illustrates the delivery of liquid by each piston of a multiple piston pump constructed for use in a liquid chromatograph according to the invention.

For a dual piston pump m=1 and hence when both pistons are delivering, their speed of advance is halved relative to that when only one piston is delivering. This is easily accomplished when the pulses for the stepping motor are derived digitally by merely switching a divide-by-two stage in or out of circuit. Where more than two pistons are provided, it may be arranged that not more than two are delivering at any one time, i.e. the situation illustrated in FIGS. 4(f)–(h), and in this case the speed of advance of the pistons is again halved when two are delivering relative to that when only one is delivering. The advantage of providing more than two pistons is that the non-delivery stroke of each piston can be extended allowing a longer period to fill the cylinder. This can be of particular advantage when a wide range of flow rates may be required and where accurate proportioning of several solvents into the cylinder is desired on each stroke. The disadvantage is, of course, greater mechanical complexity and hence cost.

An alternative arrangement, when more than two pistons are provided, is to arrange the pump so that more than one piston is always delivering e.g. with a four piston pump it could be arranged that at one time two pistons are delivering and that a third piston has an overlapping delivery. In this case the change of speed is one and a half times rather than twice and can thus be more quickly achieved, for a given acceleration, and consequently flow or pressure variations may be reduced.

Figure 2:
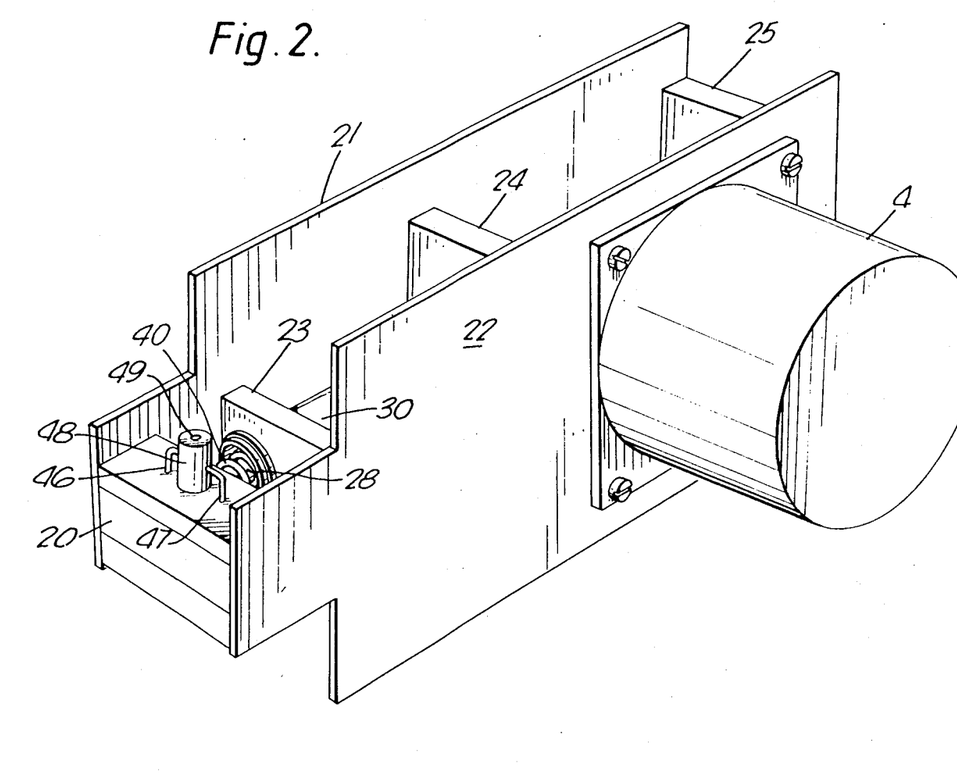
FIG. 2 is a perspective view of a pump suitable for use in the chromatograph of FIG. 1.
Figure 3:
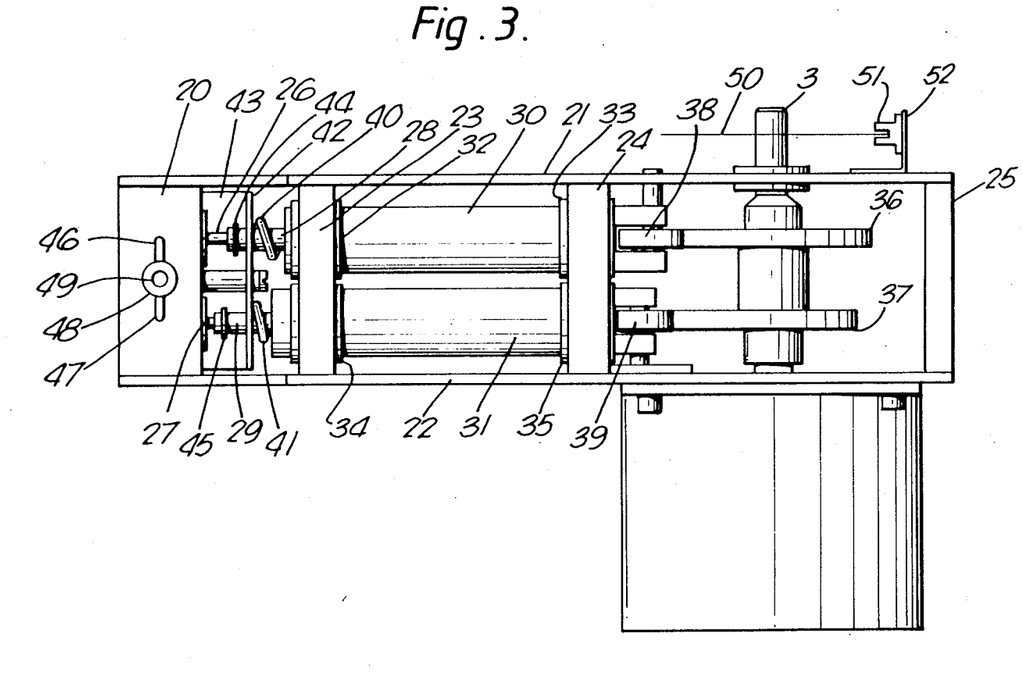
FIG. 3 is a plan view of the pump shown in FIG. 2.

FIG. 2 is a simplified perspective view of a pump 1 and motor 4 suitable for use in the chromatograph of FIG. 1 and FIG. 3 is a plan view of the pump 1 and motor 4 shown in FIG. 2.

The pump 1 comprises a pump head 20 which is clamped between two side panels 21 and 22 made from sheet steel. The pump assembly has cross pieces 23, 24 and 25 to provide a rigid structure onto which the motor 4 and various component parts of the pump are mounted. The pump 1 is provided with two pistons 26, 27 mounted in respective rods 28, 29 which pass into the interior of two tubes 30, 31. The tube 30 is slidably mounted in bearings 32, 33 in cross pieces 23 and 24 while the tube 31 is similarly mounted in bearings 34, and 35. Two cams 36 and 37 are mounted on the shaft 3 of the motor 4 and the tubes 30 and 31 are provided with respective cam followers 38 and 39. Coil springs 40 and 41 bias the cam followers 38 and 39 against the cams 36 and 37 by way of projections (not shown) on the rods 28 and 29, the rods 28 and 29 bearing against transverse members in the tubes 30 and 31. A transverse portion 42 of an L shaped bracket 43 provides a bearing surface for the other ends of the springs 40 and 41. Two circlips 44 and 45 are provided on the rods 28 and 29 to retain the pistons 26, 27 in the head 20 when the head is dismantled from the rest of the pump assembly. Two tubes 46, 47 take the outlets from each cylinder of the pump head 20 and combine them in a manifold 48 having an outlet 49 which forms the pump outlet. A shaft encoder 50 is attached to the shaft 3 of the motor 4 and a detector 51, which may be an opto electronic detector, is carried by a bracket 52 attached to the side panel 21 of the pump.

In operation the motor 4 is supplied with stepping pulses by the drive circuit 10 (FIG. 1) and causes the shaft 3 to rotate at a desired speed. Consequently the cams 36 and 37 cause the pistons 26 and 27 to advance and retract in accordance with the cam profiles which are designed to cause the pistons to advance on their delivery strokes at a constant linear velocity when the cams have a constant angular velocity. The design of such a cam profile is well known to those skilled in the art. As has been described with reference to FIG. 1 the pistons are arranged to have overlapping delivery strokes, i.e. there is a period of time during each revolution of the motor when both pistons are advancing. FIG. 4 illustrates the delivery of liquid by each piston and the motor speed at various points during a pumping cycle. FIG. 4a shows the cam angles. FIG. 4b shows the delivery cycle of piston 26 and shows that at point Ax the delivery stroke begins, i.e. the piston starts to advance, but that precompression of the liquid is occurring and no actual delivery of liquid takes place until point Ay. From point Ay until point Az delivery of liquid at a constant rate takes place since the piston is advancing at a constant linear velocity, point Az being the point at which the piston reaches top dead center and thus liquid can no longer be delivered. FIG. 4c shows the delivery cycle of piston 27, the points Bx, By and Bz corresponding to the same points on the delivery cycle of piston 27 as points Ax, Ay and Az of piston 26. It can be seen that there is an overlap between the delivery strokes of the two pistons and that consequently unless further action is taken there will be periods during which the flow rate will be doubled. This undesirable occurrence is prevented by halving the motor speed during the overlapping delivery periods as shown in FIG. 4e which illustrates the motor speed the lower lever S/2 beng equivalent to half the speed of the upper level S. The instant when simultaneous delivery by the two pistons commences is detected by monitoring the pressure at the output of the pump as is shown in FIG. 4d. When simultaneous delivery commences the pressure rises and this pressure rise is used to control the motor speed. Thus as soon as a pressure rise is detected the speed of the motor is halved and the pressure returns to the original value since the combined delivery of the two pistons is equal to that of the original single piston delivery. The end of the period during which both pumps are delivering is detected by means of detecting when one of the pistons reaches top dead centre, by use of the shaft encoder, and at that instant the motor speed is doubled to regain its original value.

FIGS. 4(f) to (j) illustrates in a similar way to FIGS. 4(b) to (e) the situation where three pistons are provided in the pump and the cam profiles are such that at any one time either one or two of the pistons is/are delivering liquid. The advantage provided by the use of three pistons operating as illustrated in FIG. 4 is that a longer period is available for filling each cylinder with the solvent which is to be pumped, i.e. the period A'z to A'x is longer than the period Az to Ax. This may be of importance when several liquids are being serially fed into each cylinder to give a desired solvent mix for pumping, particularly at high flow rates when the fill time becomes shorter since the total pump cycle time becomes shorter. Thus it becomes advantageous to make the fill time as a large proportion of the pump cycle time. Of course more than three pistons could be used giving even longer fill times but every added piston increases the mechanical complexity and hence cost.

Figure 5:
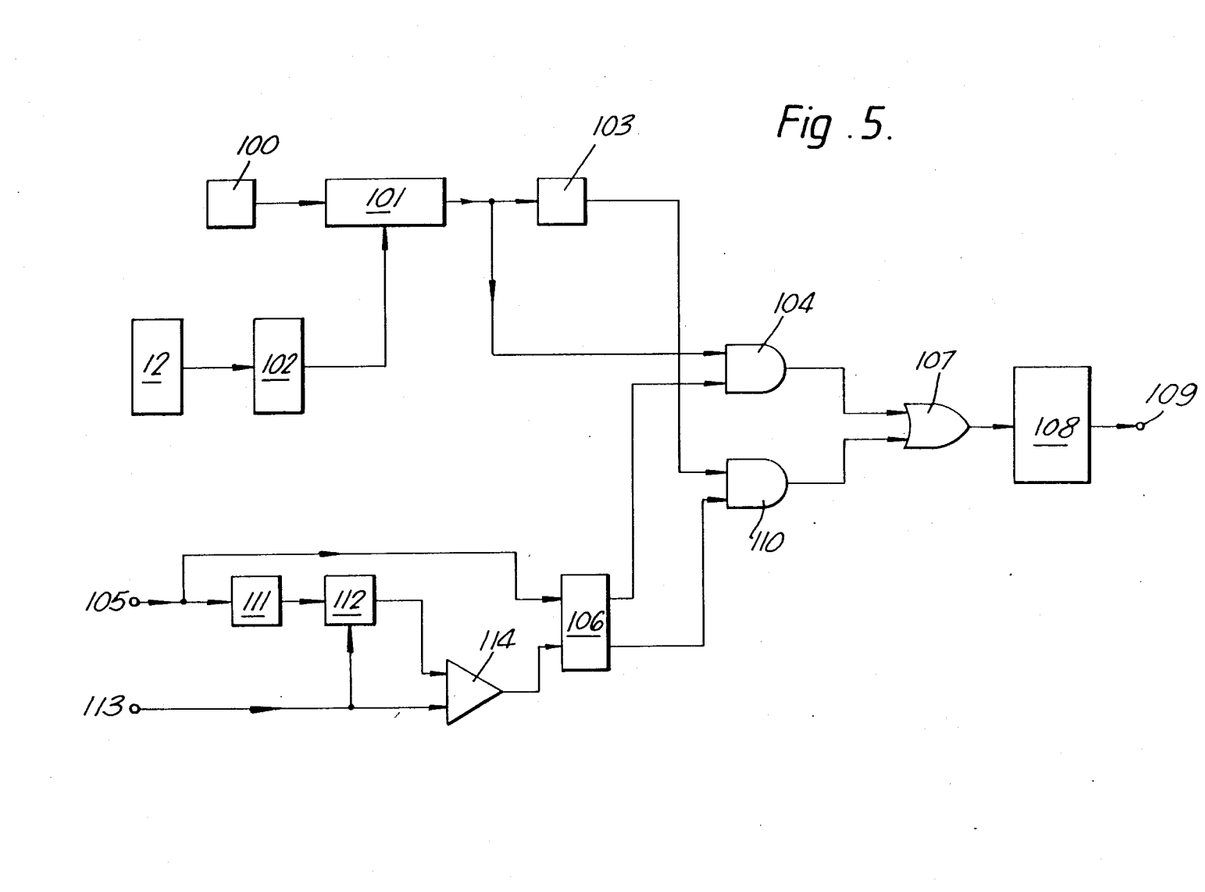
FIG. 5 is a schematic diagram of a control circuit for driving a stepping motor coupled to the pump shown in FIGS. 2 and 3.

FIG. 5 is a block schematic drawing illustrating the means of controlling the speed of the motor 4. As shown in FIG. 5 a high frequency oscillator 100 is connected to the input of a programmable divider 101. The input circuit 12 which may comprise a keyboard is connected to an encoder 102 which converts the flow rate entered on the keyboard to a code which determines an appropriate divisor for the divider 101. The encode 102 may be, for example a read only memory. The output of the divider 101 is connected to the input of a second divider 103 which divides by a factor of two and to a first input of an AND gate 104. An input terminal 105 is connected to the set input of a bistable circuit 106 whose Q output is connected to a second input of the AND gate 104. The output of the AND gate 104 is connected to a first input of an OR gate 107 whose output is fed to a driver circuit 108 which generates appropriate pulses to drive the stepper motor 4 from pulses received from the output of the OR gate 107 and supplies them to the stepper motor 4 via an output 109. The output of the second divider 103 is connected to a first input of an AND gate 110 which has a second input connected to the $\bar{Q}$ output of the bistable circuit 106 and an output connected to a second input of the OR gate 107. The input 105 is also fed via a delay circuit 111 to the sample control input of a sample and hold circuit 112. A terminal 113 is connected to a first input of a comparator 114 and to the input of the sample and hold circuit 112. The output of the sample and hold circuit 112 is connected to a second input of the comparator 114 while the output of the comparator 114 is connected to the reset input of the bistable 106.

In operation the desired flow rate is set using the input unit 12 which controls, via the encoder 102 the divisor of the divider 101 and therefore the rate at which pulses are fed to the AND gates 104 and 110. If only one piston is delivering then the bistable 106 will be set and the AND gate 104 will be enabled. Thus pulses will be fed via AND gate 104 and OR gate 107 to the driver circuit 108 which produces the appropriate driving signals for the stepper motor 4 from the pulses applied to its input. Thus the motor 4 will drive the pump at a speed which gives the required flow rate when one piston only is delivering liquid. Shortly after the instant at which one piston reaches top dead center the measured pressure which is represented by an electrical signal applied to input 113 by a pressure transducer is sampled and held in the sample and hold circuit 112. The time delay is introduced by the delay circuit 111 and is arranged to be sufficient to prevent the pressure measurement from being affected by the speed changes which take place when one piston reaches top dead center. The sampling signal at input 105 may be derived from the shaft encoder.

When both pistons start to deliver simultaneously, that is on the overlapping portions of their delivery strokes, the flow and hence the pressure at the outlet of the pump increases. At a given level the comparator 114 produces a signal at its output to reset the bistable circuit 106. The AND gate 110 is then enabled and the AND gate 104 is inhibited. Consequently the frequency of the pulses applied to the driver circuit 108 is divided by two and the motor speed is halved. When one piston subsequently reaches top dead centre the bistable circuit is set by the signal at input 105, the AND gate 104 is enabled, and AND gate 110 is inhibited thus restoring the motor speed to its original value.

FIG. 5 shows a hardware implementation of the motor speed control but it would also be possible to achieve the result using a programmed microprocessor circuit.

I claim:
1. A liquid chromatograph comprising
reciprocating pump means having multiple pistons for delivering liquid at a predetermined flow rate to a separating column, each one of said multiple pistons delivering said liquid with a delivery stroke at a rate similar to the rate of others of said multiple pistons, said multiple pistons having overlapping delivery strokes;
motor means for driving said multiple pistons; and
control means for controlling speeds of said motor means, said control means producing a control signal having a first constant value of deliveing liquid to a number m of said multiple pistons during a first period so that said number m of of multiple pistons advance at a first constant velocity, and said control signal having a second constant value for delivering liquid to a number (m+1) of said multiple pistons during a second period so that said number (m+1) of multiple pistons advance at a second constant velocity, said second constant velocity being m/(m+1) times said first constant velocity, where m is an integer and (m+1) is at most equal to a total number of pistons in said pump means.

2. A liquid chromatrograph according to claim 1, wherein said pump means has two of said multiple pistons.

3. A liquid chromatograph according to claim 1 or claim 2, wherein monitoring means are provided for monitoring pressure of said liquid delivered by said pump means, said monitoring means indicating the start of said second period by an increase of said pressure.

4. A liquid chromatograph according to claim 3, wherein said motor means drives said multiple pistons by a cam arrangement.

5. A liquid chromatograph according to claim 4, wherein said cam arrangement includes a separate cam for each one of said multiple pistons, said cam arrangement being arranged with a common shaft.

6. A liquid chromatograph according to claim 5, wherein each said separate cam includes a profiled means to produce a constant linear velocity of a respective one of said multiple pistons upon a constant angular velocity of said cam arrangement.

7. A liquid chromatograph according to claim 3, wherein said monitoring means includes means to indicate the end of said second period.

8. A liquid chromatograph according to claim 7, wherein an encoder means is disposed for indicating the positions of said multiple pistons.

9. A liquid chromatograph according to claim 1 or claim 2, wherein said motor means drives said multiple pistons by a cam arrangement.

10. A liquid chromatograph according to claim 9, wherein said cam arrangement includes a separate cam for each one of said multiple pistons, said cam arrangement being arranged with a common shaft.

11. A liquid chromatograph according to claim 10, wherein each said separate cam includes a profiled means to produce a constant linear velocity of a respective one of said multiple pistons upon a constant angular velocity of said cam arrangement.

12. A liquid chromatograph according to claim 1 or claim 2, wherein said monitoring means includes means to indicate the end of said second period.

13. A liquid chromatograph according to claim 12, wherein an encoder means is disposed for indicating the positions of said multiple pistons.

14. A liquid chromatograph according to claim 1 or claim 2, wherein said motor means include an electrical stepping motor, wherein frequency of said control signal is detected to determine said first and said second constant values, and wherein frequency of pulses of said stepping motor are divided by $(m+1)/m$ during said second period.

* * * * *